(12) United States Patent
Gennisson et al.

(10) Patent No.: US 11,234,677 B2
(45) Date of Patent: Feb. 1, 2022

(54) DETECTING APPARATUS AND ASSOCIATED KIT AND METHOD

(71) Applicants: Institut National de la Sante et de la Recherche Medicale (INSERM), Paris (FR); Centre national de la recherche scientifique, Paris (FR); Université Pierre et Marie Curie (Paris 6), Paris (FR); Université Paris Diderot—Paris 7, Paris (FR); ECOLE SUPERIEURE DE PHYSIQUE ET DE CHIMIE INDUSTRIELLES DE LA VILLE DE PARIS, Paris (FR)

(72) Inventors: Jean-Luc Gennisson, Paris (FR); Mickaël Tanter, Paris (FR); Thomas Deffieux, Paris (FR); Mathieu Pernot, Paris (FR)

(73) Assignees: INSERM (Institut National de la Santé et de la Recherche Médicale), Paris (FR); Centre National de la Recherche Scientifique (CNRS), Paris (FR); Université Pierre et Marie Curie (Paris 6), Paris (FR); Université Paris Diderot—Pris 7, Paris (FR); Ecole Superieure de Physique et de Chimie Industrielles de la Ville de Paris, Paris (FR)

(*) Notice: Subject to any disclaimer, the term of this patent is extended or adjusted under 35 U.S.C. 154(b) by 204 days.

(21) Appl. No.: 15/580,026

(22) PCT Filed: Jun. 9, 2016

(86) PCT No.: PCT/EP2016/063196
§ 371 (c)(1),
(2) Date: Dec. 6, 2017

(87) PCT Pub. No.: WO2016/198541
PCT Pub. Date: Dec. 15, 2016

(65) Prior Publication Data
US 2018/0153507 A1    Jun. 7, 2018

(30) Foreign Application Priority Data

Jun. 10, 2015    (EP) ..................................... 15305889

(51) Int. Cl.
*A61B 8/00* (2006.01)
*A61B 8/06* (2006.01)
(Continued)

(52) U.S. Cl.
CPC .............. *A61B 8/4416* (2013.01); *A61B 5/11* (2013.01); *A61B 5/1118* (2013.01); *A61B 5/24* (2021.01);
(Continued)

(58) Field of Classification Search
CPC .... A61B 8/4209; A61B 8/44; A61B 8/445–46
See application file for complete search history.

(56) References Cited

U.S. PATENT DOCUMENTS

2008/0230704 A1* 9/2008 Daghighian ......... A61B 8/0841
250/363.03
2013/0116561 A1* 5/2013 Rothberg ............. A61B 8/4254
600/438
(Continued)

FOREIGN PATENT DOCUMENTS

CN        103976709 A    8/2014
JP        2004097590 A   4/2004
(Continued)

*Primary Examiner* — Eric D. Bertram
(74) *Attorney, Agent, or Firm* — W&C IP

(57) ABSTRACT

The invention concerns a detecting apparatus (12) comprising:—at least two sensors (24, 26, 28), with at least one sensor (24) being an ultrasound transducer adapted to produce ultrasound waves, and—a positioning device (16)
(Continued)

defining several compartments (22), each compartment (22) being adapted to hold a sensor (24, 26, 28) and each compartment (22) being located at predetermined location, the positioning device (16) comprising a holder adapted to be fixed on the skull of a subject, the positioning device (16) being adapted to be maintained on the head of the subject using the holder.

2 Claims, 3 Drawing Sheets

(51) Int. Cl.
*A61B 5/11* (2006.01)
*A61B 8/08* (2006.01)
*A61B 5/24* (2021.01)
*A61B 5/291* (2021.01)

(52) U.S. Cl.
CPC ................ *A61B 5/291* (2021.01); *A61B 8/06* (2013.01); *A61B 8/0808* (2013.01); *A61B 8/4209* (2013.01); *A61B 8/481* (2013.01); *A61B 8/488* (2013.01); *A61B 2503/40* (2013.01); *A61B 2562/0209* (2013.01); *A61B 2562/0219* (2013.01); *A61B 2562/066* (2013.01); *A61B 2562/166* (2013.01)

(56) References Cited

U.S. PATENT DOCUMENTS

| | | | |
|---|---|---|---|
| 2013/0281890 A1* | 10/2013 | Mishelevich | A61N 1/361 601/2 |
| 2014/0107435 A1 | 4/2014 | Sharf et al. | |
| 2014/0121520 A1* | 5/2014 | Wang | A61B 8/403 600/444 |
| 2016/0089117 A1* | 3/2016 | Kim | A61B 8/5253 600/443 |

FOREIGN PATENT DOCUMENTS

| | | |
|---|---|---|
| JP | 2013509958 A | 3/2013 |
| WO | 2011/057028 A1 | 5/2011 |
| WO | 2014155322 A1 | 10/2014 |

* cited by examiner

DETECTING APPARATUS AND ASSOCIATED KIT AND METHOD

TECHNICAL FIELD OF THE INVENTION

The present invention concerns a detecting apparatus. The invention also relates to a kit for forming such detecting apparatus and an associated method for determining the locations of compartments adapted to hold a sensor.

BACKGROUND OF THE INVENTION

In neuroscience, a number of devices have been developed to better understand brain activity.

Usually, the developed device involves several imaging modalities allowing each to acquire a specific parameter of brain activity. Among the imaging modalities, it can be cited functional magnetic resonance imaging (also named after the acronym fMRI) related to the BOLD effect, the optical imaging (such as optical absorption imaging, acousto-optical imaging, photoacoustical imaging), functional ultrasound imaging (also named fUltrasound) and electroencephalogram.

Documents US 2014/121520 A1, US 2014/107435 A1, CN 103 976 709 A and WO 2014/155322 A1 illustrate that, in various field of medicine, systems have been developed to image an area. As a specific example, document US 2014/121520 A1 is relative to a system devoted to a patient's breast.

Nevertheless, these documents illustrate systems which are relative to area wherein the events are reproducible. These systems are thus not applicable for the brain because it is not anymore the case for the brain.

Indeed, the above-mentioned imaging modalities operate independently and cannot be achieved on the same animal at the same time to the same functional event.

Therefore, in practice, the experiments on the "almost the same" functional event are repeated and then all parameters independently acquired are treated during a post-processing method. For example, it is difficult to achieve on the same animal an fMRI imaging, coupled with a photoacoustical imaging. But the knowledge of the parameters accessible to such imaging modalities at the same time is crucial to understanding specific diseases, such as epilepsy where knowledge of functional brain activity measured by fMRI coupled with blood oxygenation level measured by an optical imaging system is extremely interesting.

SUMMARY OF THE INVENTION

The invention aims at facilitating the imaging on the same subject.

To this end, the present specification describes a detecting apparatus, the detecting apparatus comprising:
  at least two sensors, and
  a positioning device defining several compartments, each compartment being adapted to hold a sensor and each compartment being located at predetermined location,
  a sensor being an ultrasound transducer adapted to produce ultrasound waves.

Thanks to the invention, it becomes possible to image several locations on the same subject in a very easy way.

Indeed, such detecting apparatus is reconfigurable, which enables to modify the position of the sensor without modifying the position of the position device.

In addition, such detecting apparatus can be used for different experiences.

Moreover, such detecting apparatus can be useful in the cases of biological phenomena difficult to reproduce.

Notably, when the detecting apparatus comprises several sensors, several imaging modalities operating independently can be achieved on the same animal at the same time to the same functional event.

According to further aspects of the invention which are advantageous but not compulsory, the detecting apparatus might incorporate one or several of the following features, taken in any technically admissible combination:
  the positioning device is a frame having a periphery, the predetermined locations being defined with reference to the periphery.
  the compartments are removable cases or embedded at different locations.
  the detecting apparatus further comprises removable spacers having predetermined dimensions and adapted for guiding the insertion of a sensor in a compartment.
  the detecting apparatus comprises at least two sensors adapted to measure different physical quantities.
  the positioning device is a frame, the frame having a polygonal shape delimited by sides, each side having a length inferior or equal to 10 cm.
  the detecting apparatus comprises at least three sensors, one sensor being an ultrasound transducer, one sensor being an accelerometer and one sensor being adapted to measure electrical signals.
  the positioning device comprises a holder adapted to be fixed on the skull of an animal, the positioning device being adapted to be maintained on the head of an animal using the holder.
  the number of compartments is superior or equal to 100.
  the compartments are arranged in a lattice.
  the compartments are delimitated by intersecting bars, the number of bars being superior or equal to 10.
  each sensor has a sensing portion and a mechanical portion adapted to maintain the sensing portion in position and, for each sensor, the mechanical portion of one sensor has a shape which is complementary to the shape of the mechanical portion(s) of the other sensor(s).

The specification also relates to a kit for forming a detecting apparatus comprising:
  a positioning device defining several compartments, each compartment being adapted to hold a sensor and each compartment being located at predetermined location,
  a plurality of different sensors, and
  a plurality of removable spacers having predetermined dimensions and adapted for guiding the insertion of a sensor in a compartment.
  a plurality of removable spacers having predetermined dimensions and adapted for guiding the insertion of a sensor in a compartment and locking in place a sensor in a compartment.
  one sensor is a printed multielectrode electroencephalography foil.
  one sensor is one or multiple implantable electroencephalography electrodes.

The specification also relates to a method for determining the locations of compartments adapted to hold a sensor comprising:
  providing physical quantities to measure,
  providing the area where the physical quantity is to be measured,
  providing a kit as previously described,
  providing the individual dimensions of each element of the kit as previously described, and optimizing the locations of the compartments to fulfill a predetermined criteria.

According to further aspects of the invention which are advantageous but not compulsory, the method might incorporate one or several of the following features, taken in any technically admissible combination:

the criteria is that the ratio of signal to noise of each sensor be strictly superior to a given value.

the criteria is the total dimensions and weight of the detecting apparatus formed when assembling the kit.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Figure 1:
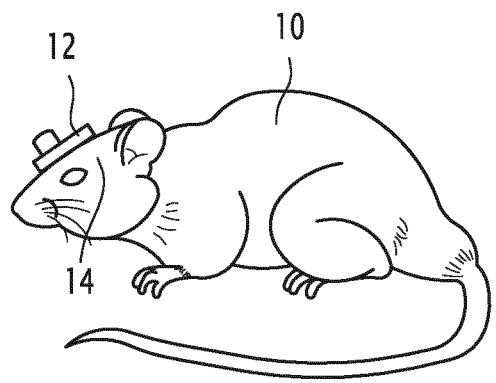
FIG. 1 shows schematically a subject holding an example of detecting apparatus.

A subject 10 and a detecting apparatus 12 are illustrated on FIG. 1.

The subject 10 is a mouse.

More generally, the subject 10 is an animal for which at least one specific area is to be analyzed.

The specific area to be analyzed depends, for instance, of the kind of biological problem that is to be studied.

As an illustration, when the biological problem is memory, the area is a specific area of the hippocampus.

For the remainder of the specification, for illustrative purpose only, it is considered that the mouse suffers from epilepsy and that the areas to be analyzed are areas of the brain.

For this, the subject 10 has a head 14, the detecting apparatus 12 being maintained on the head of the subject 10.

The detecting apparatus 12 is an apparatus adapted to detect at least one physical value in the areas of the brain of the subject 10.

The detecting apparatus 12 comprises a positioning device 16, three sensors 24, 26, 28 and three spacers 30, 32, 34.

Figure 2:
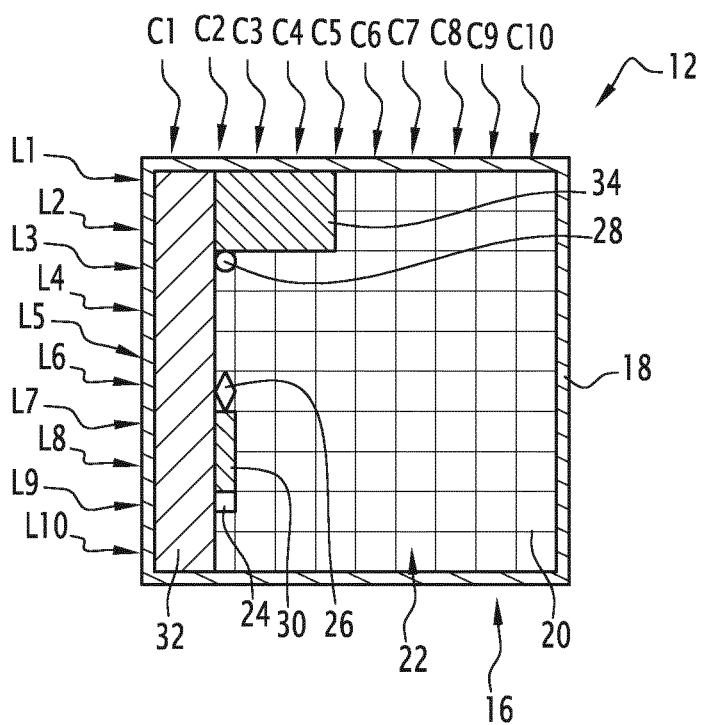
FIG. 2 shows schematically the detecting apparatus of FIG. 1.

The positioning device 16 illustrated in the example of FIG. 2 is a frame with a periphery 18 and intersecting bars 20.

According to the example illustrated, the frame has a polygonal shape delimited by sides.

As an example, the polygonal shape is a square. Each side has the same length.

For an animal considered as small, such as a rat or a mouse, the length of a side is equal to the length of the brain of the animal. For instance, the length is 1 centimeter when the subject 10 is a mouse or the length is 2 centimeters when the subject 10 is a rat.

For an animal considered as big, such as a human, the length of a side is equal to a portion of the length of the brain of the animal. For instance, the length of the side is inferior to 10 centimeters.

More generally, the length of a side is equal to the minimum of the length of the brain of the animal and 10 centimeters.

For the specific case of FIG. 1, each side has a length inferior or equal to 10 centimeters (cm).

The intersecting bars 20 constitute a grid.

The number of bars 20 is superior or equal to 10.

In the specific example of FIG. 2, ten horizontal bars 20 and ten vertical bars 20 are illustrated.

Accordingly, ten rows and ten columns can be defined with the periphery 18.

In the remainder of the specification, the rows are labeled L with a number so that each row is labeled L1, L2, L3, L4, L5, L6, L7, L8, L9 or L10.

Similarly, in the remainder of the specification, the columns are labeled C with a number so that each column is labeled C1, C2, C3, C4, C5, C6, C7, C8, C9 or C10.

In addition, the words "up" and "down" on the one hand and "left" and "right" on the other hand are defined with reference respectively to the rows L1, L2, L3, L4, L5, L6, L7, L8, L9, L10 and to the columns C1, C2, C3, C4, C5, C6, C7, C8, C9, C10.

It will be consider that the less high the number associated to the row L1, L2, L3, L4, L5, L6, L7, L8, L9, L10 is the upper the row L1, L2, L3, L4, L5, L6, L7, L8, L9, L10 is. In other words, the first row L1 is above the second row L2 while the second row L2 is below the first row L1. Similarly, the first column C1 is on the left of the second column C2 while the second column C2 is on the right of the first column C1.

The intersecting bars 20 are delimitating compartments 22 which are defined for the positioning device 16.

In the illustrated example, the positioning device defines a number of compartments 22 which is equal to 100.

More generally, the positioning device 16 defines a number of compartments 22 which is superior or equal to 100.

Each compartment 22 is adapted to hold a sensor.

Each compartment 22 is located at a predetermined location.

In the illustrated example, the predetermined locations are defined with reference to the periphery 18.

For instance, each compartment 22 can be linked in a one-to-one manner to two coordinates: one row coordinate and one column coordinate. As an example, the compartment 22 belonging to the first row L1 and the first column C1 is a neighbor for the compartment 22 belonging to the first row L1 and the second column C2, the compartment 22 belonging to the second row L2 and the first column C1 and the compartment 22 belonging to the second row L2 and the second column C2.

In such specific case, the compartments 22 are arranged in a lattice. Such lattice is a regular lattice.

In addition, the spatial distance between two adjacent predetermined locations is inferior or equal to 100 µm.

Preferably, the spatial distance between two adjacent predetermined locations is inferior or equal to 10 µm.

For instance, for each compartment 22, a center is defined. The predetermined location of a compartment 22 then corresponds to the center of the considered compartment 22.

In such context, the spatial distance between two predetermined locations is defined as the distance between the corresponding centers.

Furthermore, the positioning device 16 comprises a holder.

The positioning device is adapted to be maintained on the head 14 of the subject 10 using the holder.

This means that the holder is adapted to be fixed on the skull of the subject 10.

The first sensor 24 is an ultrasound transducer adapted to produce ultrasound waves.

According to a specific example, the first sensor 24 is a high frequency ultrasound transducer. In such case, the first sensor 24 is a linear array adapted to operate at a frequency around 15 MHz (MegaHertz).

The first sensor 24 is used mainly to detect cerebral blood volume and flow through Doppler sequences or contrast agents.

The first sensor 24 is located on the second column C2 and on the ninth row L9.

More precisely, the first sensor 24 is located on the upper part on the right of the compartment 22 belonging to the second column C2 and the ninth row L9.

The second sensor 26 is an accelerometer.

An accelerometer is adapted to measure proper acceleration of the animal. The accelerometer can be used to detect the state of the animal. The state of the animal is, for instance sleeping, running or eating. The knowledge of such state is, for example, useful for behavioral studies.

The second sensor 26 is located on the second column C2 and on the sixth row L6.

More precisely, the second sensor 26 is located on the right of the compartment 22 belonging to the second column C2 and the sixth row L6.

The third sensor 28 is adapted to measure electrical signals.

For instance, the third sensor 28 is a voltmeter.

According to other embodiments, the third sensor 28 is a surface electrode, an implanted electrode or an array of such electrodes.

The third sensor 28 is located on the second column C2 and on the third row L3.

More precisely, the third sensor 28 is located on the upper part on the right of the compartment 22 belonging to the second column C2 and the third row L3.

Each spacer 30, 32, 34 is removable.

By "removable", it is meant that each spacer 30, 32, 34 can be placed at a specific location and then moved to another location.

Each spacer 30, 32, 34 has predetermined dimensions.

The first spacer 30 has a parallelepiped shape, the first spacer 30 occupying half a column along one dimension and two rows according to the other dimension.

The second spacer 32 has a parallelepiped shape, the second spacer 32 occupying one column and a half along one dimension and ten rows according to the other dimension.

The third spacer 34 has a parallelepiped shape, the third spacer 32 occupying three columns along one dimension and two rows according to the other dimension.

Each spacer 30, 32, 34 is adapted for guiding the insertion of a sensor in a compartment 22.

In the illustrated example of FIG. 2, the first spacer 30 is on the right of the compartments 22 belonging respectively to the second column C2 and the fifth row L5 and to the second column C2 and the sixth row L6.

The first spacer 30 is adapted to guide the first sensor 24 and the second sensor 26.

The second spacer 32 is situated on the first column C1 and on the left of the second column C2.

The second spacer 32 is adapted to guide each sensor 24, 26 and 28.

As can be seen on FIG. 2, the third spacer 34 is on the compartments 22 belonging respectively to the third column C3 and the first row L1, to the third column C3 and the second row L2, to the fourth column C4 and the first row L1, to the fourth column C4 and the second row L2. The third spacer 34 is also located on the right of the compartments 22 belonging to the second column C2 and the first row L1 and to the second column C2 and the second row L2. The third spacer 34 is also located on the left of the compartments 22 belonging to the fifth column C5 and the first row L1 and to the fifth column C5 and the second row L2.

The third spacer 34 is adapted to guide the third sensor 28.

Figure 3:
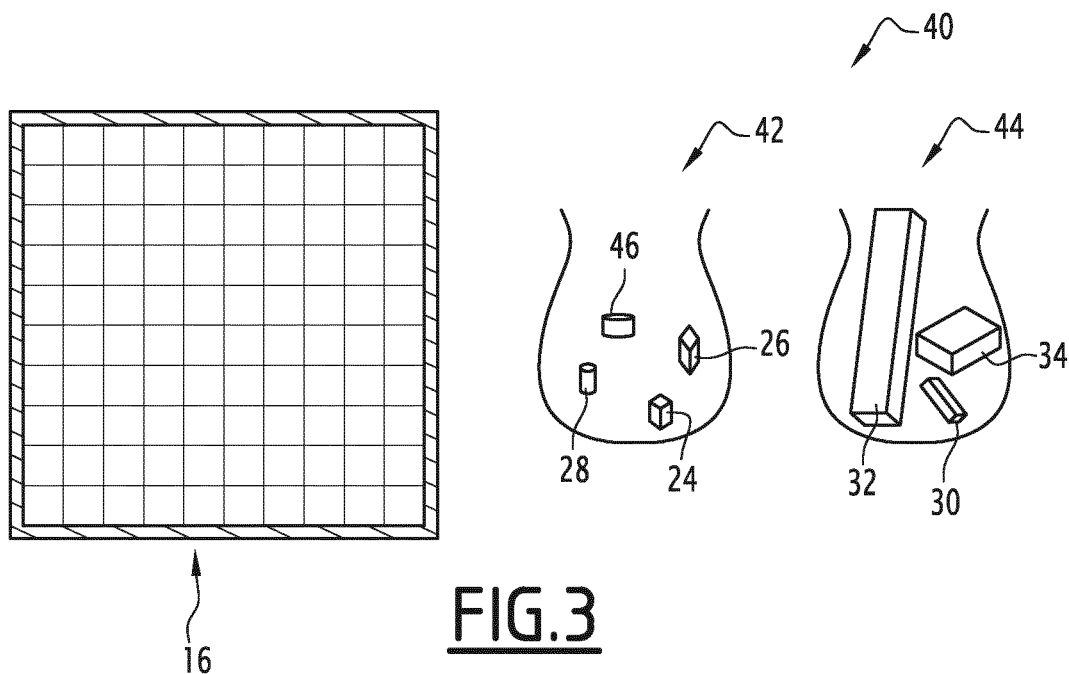
FIG. 3 shows schematically a kit for forming the detecting apparatus of FIG. 1.

The detecting apparatus 12 is reconfigurable as can be illustrated on the kit 40 for forming detecting apparatuses 12 which is illustrated on FIG. 3.

The kit 40 comprises the positioning device 16, a sensor bag 42 and a spacer bag 44.

The sensor bag 42 comprises the first sensor 24, the second sensor 26, the third sensor 28 and a fourth sensor 46.

According to this specific embodiment, the fourth sensor 46 is a temperature sensor.

Alternatively, the fourth sensor 46 is an optical sensor.

The spacer bag 44 comprises the three spacers 30, 32 and 34.

Operation of the kit 40 is now described in reference to an example of carrying out of a method for determining the locations of compartments 22 being adapted to hold a sensor.

The method comprises a step of providing physical quantities to measure.

For instance, it may be desired to measure the temperature, the blood flux, the proper acceleration and electric activity.

The method comprises a step of providing the area where each physical quantity is to be measured.

In the example illustrated, the area is a spatial zone of the brain of the subject 10.

The method comprises a step of providing the kit 40.

The method also comprises a step of providing the individual dimensions of each element 16, 24, 26, 28, 30, 32, 34 and 46 of the kit 40.

For instance, for the first spacer 30, the following data are provided: the first spacer 30 has a parallelepiped shape, the first spacer 30 occupying half a column along one dimension and two rows according to the other dimension.

The method also comprises a step of optimizing the locations of the compartments 22 to fulfill a predetermined criteria.

By way of an illustration, the optimizing step is performed by a series of iterations in an optimization program. The goal of this optimization program, starting from an initial configuration of the locations is to obtain a configuration of locations of the compartments 22 that confer to the detecting apparatus 12 a property that as much as possible fulfills the criteria.

For this, a cost function C representative of deviations of the detecting apparatus 12 from the ideal apparatus fulfilling the criteria is used.

The cost function C is a positive function that should be minimized during the step of optimizing.

In order to proceed with performing this minimization, it is sufficient to start from initial configuration of the locations and to use a calculation method that provides the ability to reduce by iterations the value of the cost function C.

As illustration, the calculation method used is a damped least squares method (often referred to by the English acronym DLS for "damped least-squares").

The configuration of locations of the compartments 22 are thus obtained after iterations of the optimization program.

The predetermined criteria to be considered at the step of optimizing is, for instance, that the ratio of signal to noise of each sensor 24, 26, 28 and 46 be strictly superior to a given value.

Alternatively, the predetermined criteria is the total dimensions and weight of the kit 40 when assembled. In other words, the predetermined criteria is the total dimensions and weight of the detecting apparatus 12 formed when assembling the kit 40.

Then, with the configuration of locations of the compartments 22, a new detecting apparatus 12 may be obtained.

Figure 4:
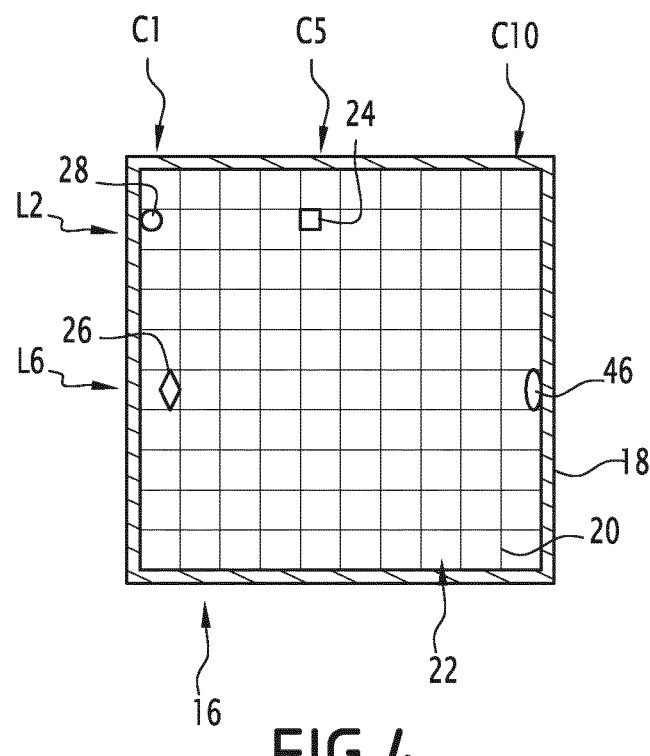
FIG. 4 shows schematically another example of detecting apparatus that can be obtained with the kit of FIG. 3.

FIG. 4 illustrates another example of detecting apparatus 12 that can be obtained.

The detecting apparatus 12 comprises the positioning device 16 and the four sensors 24, 26, 28 and 46.

In this specific embodiment, the detecting apparatus 12 does not comprise any spacer.

The first sensor 24 is located on the fifth column C5 and on the second row L2.

More precisely, the first sensor 24 is located on the upper part on the left of the compartment 22 belonging to the fifth column C5 and on the second row L2.

The third sensor 26 is located on the first column C1 and on the sixth row L6.

More precisely, the third sensor 26 is located on the upper part on the right of the compartment 22 belonging to the first column C1 and on the sixth row L6.

The third sensor 28 is located on the first column C1 and on the second row L2.

More precisely, the third sensor 28 is located on the upper part on the left of the compartment 22 belonging to the first column C1 and on the second row L2.

The fourth sensor 46 is located on the tenth column C10 and on the sixth row L6.

More precisely, the fourth sensor 46 is located on the upper part on the right of the compartment 22 belonging to the tenth column C10 and on the sixth row L6.

It should be understood that multiple detecting apparatus 12 are obtainable with the kit 40.

According to another embodiment, the detecting apparatus 12 comprises only two sensors.

In such case, preferably, the two sensors are adapted to measure different physical quantities Alternatively, more than one sensor is an ultrasound transducer.

In other word, it becomes possible to image several locations on the same subject 10 in a very easy way.

Indeed, the detecting apparatus 12 is reconfigurable, which enables to modify the position of the sensors 24, 26, 28 and 46 without modifying the position of the position device 16.

In addition, such detecting apparatus 12 can be used for different experiences.

Moreover, such detecting apparatus 12 can be useful in the cases of biological phenomena difficult to reproduce.

For instance, thanks to such detecting apparatus 12, several different physical quantities can be measured simultaneously on the same subject 10 when this subject 10 is facing an epilepsy crisis.

Figure 5:
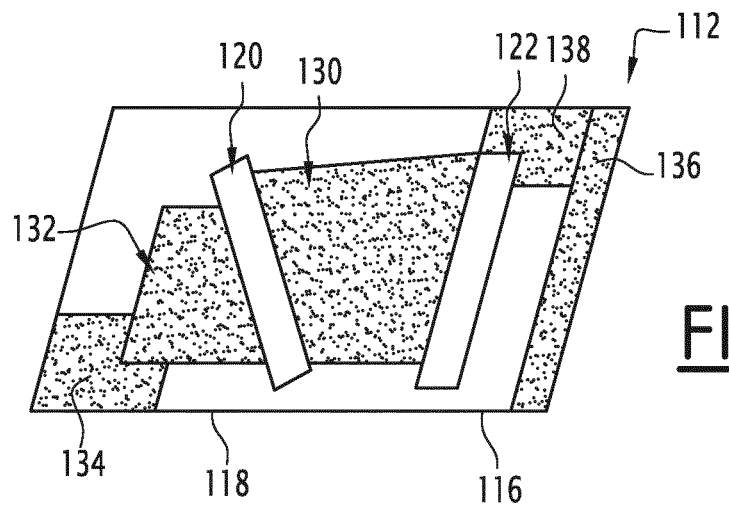
FIG. 5 shows schematically another example of detecting apparatus.
Figure 6:
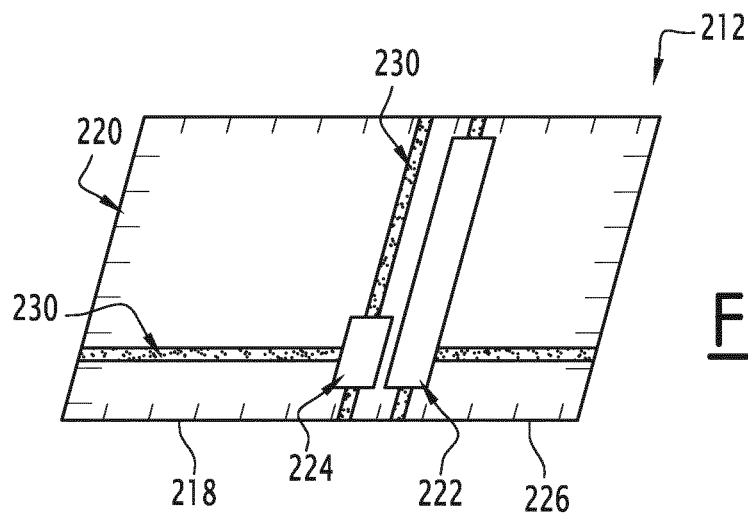
FIG. 6 shows schematically another example of detecting apparatus.
Figure 7:
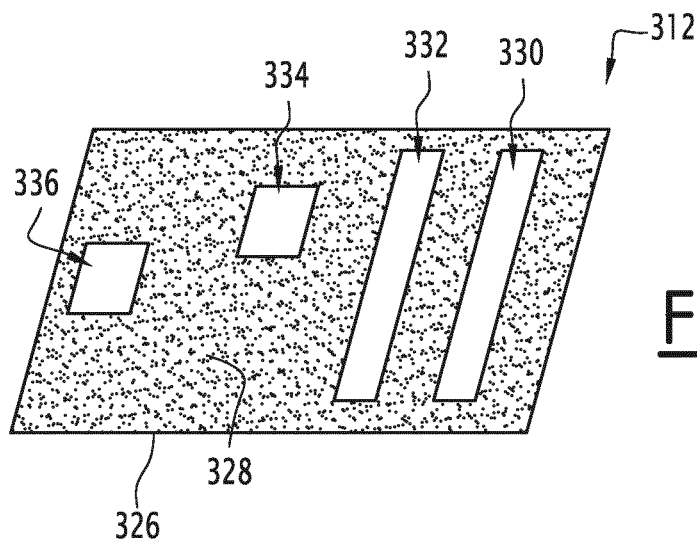
FIG. 7 shows schematically another example of detecting apparatus.

FIGS. 5 to 7 illustrates other examples of detecting apparatuses that may be considered.

On FIG. 5, a detecting apparatus 112 is illustrated.

The detecting apparatus 112 comprises a positioning device 116 which is a frame with a periphery 118.

The detecting apparatus 112 comprises a first ultrasound probe 120 and a second ultrasound probe 122.

The detecting apparatus 112 comprises removable spacers 130, 132, 134, 136 and 138.

The remarks made for an element with reference to FIG. 1 apply in a similar to the same element in the embodiment of FIG. 5.

The detecting apparatus 112 combines both ultrasound probes 120 and 122 over different selected brain areas. For example, the sensors 120 and 122 are positioned using spacers 130, 132, 134, 136 and 138.

On FIG. 6, another detecting apparatus 212 is illustrated.

The detecting apparatus 212 comprises a positioning device 216 which is a frame with a periphery 218 and a grid 220.

The detecting apparatus 212 comprises an ultrasound probe 222 and an implanted electrode array 224.

The detecting apparatus 212 also comprises rods 230 for positioning the sensors 222 and 224.

The remarks made for an element with reference to FIG. 1 apply in a similar to the same element in the embodiment of FIG. 6.

The detecting apparatus 212 combines the ultrasound probe 222 and the implanted electrode array 224 in the context of epilepsy monitoring on awake rats. For example, the sensors 222 and 224 are positioned using the rods 230 on the grid 220.

On FIG. 7, another detecting apparatus 312 is schematically shown.

The detecting apparatus 312 comprises a positioning device 326 which is a frame. The frame is obtained by three-dimensional printing. Such technique is a specific example of rapid prototyping technique.

The detecting apparatus 312 further comprises two ultrasound probes 330, 332, one accelerometer 334 and one surface electrode 336.

Each sensor 330, 332, 334 and 336 are embedded in the printed frame.

The remarks made for an element with reference to FIG. 1 apply in a similar to the same element in the embodiment of FIG. 7.

The detecting apparatus 312 is, for instance, usable in the context of functional connectivity and behavioral study in awake mice.

According to another example, each sensor 24, 26, 28 has a sensing portion and a mechanical portion adapted to maintain the sensing portion in position. In addition, for each sensor, the mechanical portion of one sensor 24, 26, 28 has a shape which is complementary to the shape of the mechanical portions of the other sensors 24, 26, 28.

In other words, the cooperation between two mechanical portions of two different sensors 24, 26, 28 enables to maintain each sensing portion in position and to reduce the congestion.

For instance, each mechanical portion has a recess and a protusion, the shape of the protusion being complementary to the shape of the recess. Thus, the protusion of one mechanical portion can be inserted in the recess of the adjacent mechanical portion so as to enable the maintaining of each sensor 24, 26, 28. In addition, in such example, the mechanical portion can be identical which results in an easier fabrication.

In such embodiment, each sensor 24, 26, 28 can be imbricated one in another.

According to a specific embodiment, one sensor 24 is an ultrasound transducer while one sensor 26 is a printed multielectrode electroencephalography (EEG) foil. The foil is positioned below the ultrasound transducer compartment, that is nearer to the area to be sensed.

In this case, the foil is proximal to the brain while the ultrasound transducer is distal to the brain. In such context, proximal and distal are defined with relation to the brain. In other words, a proximal element is nearer to the brain than a distal element.

According to another embodiment, one sensor 24 is an ultrasound transducer while one sensor 26 is one or multiple implantable electroencephalography (EEG) electrodes.

These electrodes are guided obliquely inside the brain. In addition, these electrodes are below the ultrasound transducer compartment, which means nearer to the area to be sensed.

In this case, the electrodes are proximal to the brain while the ultrasound transducer is distal to the brain. In such context, proximal and distal are defined with relation to the brain. In other words, a proximal element is nearer to the brain than a distal element.

The embodiments and alternative embodiments considered here-above can be combined to generate further embodiments of the invention.

In addition, the detecting apparatus 12 may be used for various uses.

Three uses are developed below.

First Use: Imaging a Specific Area of the Brain of a Mobile Rat with a Camera

According to the first use, the detecting apparatus 12 is adapted to image a specific plane of the mobile rat with an embedded camera.

A frame is implanted on a rat with screws and dental cement. The skull of the rat is rendered thinner or opened on a window.

In a first embodiment, the position of the frame is determined before thanks to an anatomical frame. Superficial veins of the brain or skull suture lines are examples of anatomical frame.

According to another embodiment, after putting the frame on the skull of the rat, the precise location of the frame is determined thanks to an anatomical frame, such as superficial veins of the brain as previously proposed.

According to still another embodiment, after putting the frame on the skull of the rat, the precise location of the frame is determined thanks to a specific sensor. This specific sensor has a known position with relation to the frame. Such known position can be obtained by using a compartment adapted to hold the sensor. In specific cases, the compartment is translated to obtain a more precise estimation of the position of the frame.

The area to be imaged is then determined. As an example, the determined area is the visual cortex.

The kind of additional sensor to be fixed and the associated location are chosen.

As an example, the additional sensor is a camera.

In variant, the additional sensor is an accelerometer or a microphone.

According to the case, the additional sensor is put on the compartment corresponding to the chosen associated location or the additional sensor is put in a removable case which is then positioned at the associated location.

If a removable case is used, the detecting apparatus 12 only comprises the additional sensor during the experiment which enables the rat to move relatively freely.

The only constraint is that the rat moves with the frame.

In such first use, the detecting apparatus 12 has two sensors: a probe and a camera. The probe is positioned in a stereotactic way with relation to the brain of the rat. The position of the camera, and more generally the second sensor, is reconfigurable as well as the choice of the nature of the sensor. The position of the second sensor is determined by using the position of the first sensor. It should be noted that the position of the second sensor may be subjected to less strict constraints that the position of the first sensor in so far as the area to be imaged may be relatively large whereas the position of the first sensor is imposed a stereotactic way with relation to the brain of the rat Second Use: Imaging Two Specific Areas of the Brain of a Mobile Rat with Two Probes According to the second use, two planes of the brain of a mobile rat are imaged with two ultrasound probes.

A frame is implanted on a rat with screws and dental cement. The skull of the rat is rendered thinner or opened on a window.

In a first embodiment, the position of the frame is determined before thanks to an anatomical frame. Superficial veins of the brain or skull suture lines are examples of anatomical frame.

According to another embodiment, after putting the frame on the skull of the rat, the precise location of the frame is determined thanks to an anatomical frame, such as superficial veins of the brain as previously proposed.

According to still another embodiment, after putting the frame on the skull of the rat, the precise location of the frame is determined thanks to a specific sensor. This specific sensor has a known position with relation to the frame. Such known position can be obtained by using a compartment adapted to hold the sensor. In specific cases, the compartment is translated to obtain a more precise estimation of the position of the frame.

The areas to be imaged are then determined. As an example, the determined area can be the visual cortex and the olfactory bulb.

For this second use, it is assumed that several compartments are positioned in a stereotactic way with relation to the brain of the rat.

According to an embodiment, such compartments are not removable and are positioned with the frame.

According to another embodiment, the compartments are removable and are positioned by using one of the previous proposed methods for positioning the frame. As an example, the precise location of a compartment is determined thanks to a specific sensor The ultrasound probes are assembled in a transitory way with the compartments which correspond to the desired location.

This enables to cumulate several advantages.

On the one hand, the rat only holds the ultrasound probes during the experiment.

On the other hand, both the frame and the ultrasound probes are positioned in a stereotactic way with relation to the brain of the rat.

In other words, the use of the detecting apparatus 12 in such context really renders carrying out an in vivo experiment on the brain of a rat easier for the scientist, without loss of precision in the measurements to be achieved on the rat.

Third Use: Imaging a Unique Area of the Brain of a Mobile Mouse and Using an Array of Surface EEG Multielectrodes Such as Printed Foil According to the third use, only one plane of the brain of a mobile mouse is imaged with a probe while enabling the simultaneous use of an array of surface EEG multielectrodes.

A frame is implanted on a mouse with screws and dental cement. The skin of the mouse is removed.

In a first embodiment, the position of the frame is determined before thanks to an anatomical frame. Superficial veins of the brain or skull suture lines are examples of anatomical frame.

According to another embodiment, after putting the frame on the skull of the mouse, the precise location of the frame is determined thanks to an anatomical frame, such as superficial veins of the brain as previously proposed.

According to still another embodiment, after putting the frame on the skull of the mouse, the precise location of the frame is determined thanks to a specific sensor. This specific sensor has a known position with relation to the frame. Such known position can be obtained by using a compartment adapted to hold the sensor. In specific cases, the compartment is translated to obtain a more precise estimation of the position of the frame.

The area to be imaged is then determined. As an example, the determined area is the hippocampus. The ultrasound probe is assembled in a transitory way with the compartment which corresponds to the desired location.

For this third use, it is assumed that a second compartment adapted to receive an array of surface EEG multielectrodes such as printed foil is first positioned in a stereotactic way with relation to the brain of the mouse and then glued with a mix of EEG paste and glue to the skull.

According to an embodiment, such printed foil is positioned with the frame below the ultrasound probe compartment.

In variant, the additional sensor is an EEG electrode that is guided obliquely inside the brain below the ultrasound probe.

In this third use, the same advantages as detailed for the second use still apply.

In each use, it appears that the detecting apparatus 12 has two main interests which may be cumulated in the use.

The first interest is the fact that the detecting apparatus 12 is reconfigurable by construction which enables to change the detecting apparatus 12 easily for the scientist.

One advantage is that each additional sensor can be chosen and/or positioned according to the specific needs of the experiment.

One advantage resulting from such reconfigurability is that the weight applied on the skull of the rat is limited to the time of acquisition. The useful sensor(s) is only hold for a limited time.

The second interest is the fact that the detecting apparatus 12 is adapted for achieving brain imaging of a small animal, such as a rat.

Notably, the detecting apparatus 12 enables to ensure that several sensors are positioned in a stereotactic way with relation to the brain of the rat.

This positioning in a stereotactic way is in addition compatible with the movement of the rat.

The invention claimed is:

1. A method for imaging a brain of a subject, comprising:
providing a detecting apparatus comprising
a set of sensors, the set of sensors including at least two sensors or emitters, with at least one sensor or emitter being an ultrasound transducer adapted to produce ultrasound waves, and
a holder having a periphery and defining several compartments, each compartment being adapted to hold a sensor or an emitter of the set of sensors and each compartment being located at a predetermined location, the predetermined location being defined with reference to the periphery of the holder, the holder being adapted to be maintained on a head of a subject in a fixed position,
maintaining the holder on a head of the subject;
modifying a position of the at least one sensor or emitter without modifying a position of the holder;
imaging at least a portion of the brain of the subject using at least one sensor, and
guiding insertion of a sensor in a compartment of the several compartments using removable spacers of predetermined dimensions.

2. A method for imaging a brain of a subject, comprising:
providing a detecting apparatus comprising
a set of sensors, the set of sensors including at least two sensors or emitters, with at least one sensor or emitter being an ultrasound transducer adapted to produce ultrasound waves, and
a holder having a periphery and defining several compartments, each compartment being adapted to hold a sensor or an emitter of the set of sensors and each compartment being located at a predetermined location, the predetermined location being defined with reference to the periphery of the holder, the holder being adapted to be maintained on a head of a subject in a fixed position,
maintaining the holder on a head of the subject;
modifying a position of the at least one sensor or emitter without modifying a position of the holder; and
imaging at least a portion of the brain of the subject using at least one sensor,
wherein the compartments are arranged in a lattice, and
wherein the compartments are delimited by intersecting bars, the number of bars being greater than or equal to 10.

* * * * *